(12) United States Patent
Biedermann et al.

(10) Patent No.: US 9,173,684 B2
(45) Date of Patent: Nov. 3, 2015

(54) RECEIVING PART FOR RECEIVING A ROD FOR COUPLING THE ROD TO A BONE ANCHORING ELEMENT AND BONE ANCHORING DEVICE WITH SUCH A RECEIVING PART

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 47 days.

(21) Appl. No.: 13/323,420

(22) Filed: Dec. 12, 2011

(65) Prior Publication Data
US 2012/0179211 A1 Jul. 12, 2012

Related U.S. Application Data (60) Provisional application No. 61/421,967, filed on Dec. 10, 2010.

(30) Foreign Application Priority Data

Dec. 10, 2010 (EP) ..................................... 10194607

(51) Int. Cl.
*A61B 17/70* (2006.01)
(52) U.S. Cl.
CPC .................................. *A61B 17/7037* (2013.01)
(58) Field of Classification Search
CPC ................................................ A61B 17/7037
USPC .................. 606/264–278, 300, 305–308, 328
See application file for complete search history.

(56) References Cited

U.S. PATENT DOCUMENTS 4,552,387 A * 11/1985 Schmidt .......................... 285/238
4,946,458 A * 8/1990 Harms et al. ................... 606/305
(Continued)

FOREIGN PATENT DOCUMENTS

CN 2474098 Y 1/2002
CN 2486118 Y 4/2002
(Continued)

OTHER PUBLICATIONS

European Search Report for European Application No. 10 194 607.7, European Search Report dated Mar. 24, 2011 and Apr. 1, 2011 (6 pgs.).

(Continued)

*Primary Examiner* — Kevin T Truong
*Assistant Examiner* — Tracy Kamikawa
(74) *Attorney, Agent, or Firm* — Christie, Parker & Hale, LLP (57) ABSTRACT

A receiving part for coupling a rod to a bone anchoring element includes a receiving part body including a head receiving portion having an open end and a first exterior surface portion, the head receiving portion being flexible to allow introduction and clamping of a head of a bone anchoring element, and a locking ring having a first interior surface portion configured to engage the first exterior surface portion of the head receiving portion in a first contact region to lock an angular position of the head, wherein the first interior surface portion is spaced apart from an end of the locking ring, and wherein one of the first exterior surface portion or the first interior surface portion includes a cylindrical surface, and the other one of the first exterior surface portion or the first interior surface portion includes another cylindrical surface or a ring-shaped bulge portion.

22 Claims, 6 Drawing Sheets

(56) References Cited

U.S. PATENT DOCUMENTS

| | | | |
|---|---|---|---|
| 5,549,608 A * | 8/1996 | Errico et al. | 606/264 |
| 5,575,792 A * | 11/1996 | Errico et al. | 606/276 |
| 5,578,033 A * | 11/1996 | Errico et al. | 606/276 |
| 5,584,834 A * | 12/1996 | Errico et al. | 606/264 |
| 5,586,984 A * | 12/1996 | Errico et al. | 606/264 |
| 5,609,593 A * | 3/1997 | Errico et al. | 606/276 |
| 5,733,285 A | 3/1998 | Errico et al. | |
| 6,355,040 B1 | 3/2002 | Richelsoph et al. | |
| 7,699,876 B2 * | 4/2010 | Barry et al. | 606/266 |
| 8,002,806 B2 * | 8/2011 | Justis | 606/264 |
| 8,192,470 B2 * | 6/2012 | Biedermann et al. | 606/265 |
| 8,197,519 B2 * | 6/2012 | Schlaepfer et al. | 606/278 |
| 8,506,609 B2 * | 8/2013 | Biedermann et al. | 606/306 |
| 8,506,610 B2 * | 8/2013 | Biedermann et al. | 606/308 |
| 2001/0047173 A1 * | 11/2001 | Schlapfer et al. | 606/72 |
| 2005/0080415 A1 * | 4/2005 | Keyer et al. | 606/61 |
| 2005/0096653 A1 | 5/2005 | Doubler et al. | |
| 2005/0277927 A1 | 12/2005 | Guenther et al. | |
| 2006/0200128 A1 | 9/2006 | Mueller | |
| 2008/0027432 A1 * | 1/2008 | Strauss et al. | 606/61 |
| 2008/0108992 A1 | 5/2008 | Barry et al. | |
| 2008/0161859 A1 | 7/2008 | Nilsson | |
| 2008/0269742 A1 * | 10/2008 | Levy et al. | 606/60 |
| 2009/0036934 A1 * | 2/2009 | Biedermann et al. | 606/301 |
| 2009/0149887 A1 * | 6/2009 | Schlaepfer et al. | 606/278 |
| 2010/0131017 A1 * | 5/2010 | Farris et al. | 606/308 |
| 2010/0160975 A1 * | 6/2010 | Biedermann et al. | 606/302 |
| 2010/0160976 A1 * | 6/2010 | Biedermann et al. | 606/302 |
| 2010/0168800 A1 * | 7/2010 | Biedermann et al. | 606/302 |
| 2010/0168801 A1 * | 7/2010 | Biedermann et al. | 606/302 |
| 2011/0112582 A1 * | 5/2011 | Abdelgany | 606/267 |
| 2011/0276098 A1 * | 11/2011 | Biedermann et al. | 606/305 |
| 2012/0095516 A1 * | 4/2012 | Dikeman | 606/305 |
| 2012/0165874 A1 * | 6/2012 | Biedermann et al. | 606/278 |
| 2012/0172932 A1 * | 7/2012 | Biedermann et al. | 606/279 |
| 2012/0179209 A1 * | 7/2012 | Biedermann et al. | 606/305 |
| 2012/0283789 A1 * | 11/2012 | Biedermann et al. | 606/308 |
| 2013/0085536 A1 * | 4/2013 | Biedermann et al. | 606/308 |
| 2013/0096623 A1 * | 4/2013 | Biedermann et al. | 606/279 |
| 2013/0123860 A1 * | 5/2013 | Biedermann et al. | 606/305 |
| 2013/0123861 A1 * | 5/2013 | Biedermann et al. | 606/305 |

FOREIGN PATENT DOCUMENTS

| | | |
|---|---|---|
| EP | 2 191 780 A1 | 6/2010 |
| EP | 2 201 903 A1 | 6/2010 |
| EP | 2 204 129 A1 | 7/2010 |
| JP | 2007-510468 A | 4/2007 |
| JP | 2009-540872 A | 11/2009 |
| WO | WO 2005/041821 A2 | 5/2005 |
| WO | WO 2007/038350 A2 | 4/2007 |
| WO | WO 2008/103150 A1 | 8/2008 |

OTHER PUBLICATIONS

Chinese Office action for Application No. 201110409048.4, dated Nov. 25, 2014, 11 pages.

* cited by examiner

RECEIVING PART FOR RECEIVING A ROD FOR COUPLING THE ROD TO A BONE ANCHORING ELEMENT AND BONE ANCHORING DEVICE WITH SUCH A RECEIVING PART

CROSS-REFERENCE TO RELATED APPLICATION(S)

The present application claims the benefit of U.S. Provisional Patent Application Ser. No. 61/421,967, filed Dec. 10, 2010, the contents of which are hereby incorporated by reference in their entirety, and claims priority to European Patent Application EP 10 194 607.7, filed Dec. 10, 2010, the contents of which are hereby incorporated by reference in their entirety.

BACKGROUND

1. Field of the Invention

The invention relates to a receiving part for receiving a rod for coupling the rod to a bone anchoring element and a bone anchoring device with such a receiving part. The head of the bone anchoring element can be locked in the receiving part by compression of a head receiving portion by means of a locking ring, which laterally surrounds the head receiving portion. The head receiving portion has an exterior surface portion and the locking ring has an interior surface portion that engages the exterior surface portion in a contact region to clamp the head. At least one of the exterior and the interior surface portion may be cylindrical and the other one may be either cylindrical or a ring-shaped bulge. The bone anchoring device can be realized, for example, in the form of a polyaxial bone screw, allowing for pivotal movement of the head and a locking of the head in a desired angular position.

2. Description of Related Art

U.S. Pat. No. 5,733,285 describes a polyaxial colletted locking mechanism for use with an orthopaedic apparatus, which includes a screw having a curvate head and a coupling element. The coupling element has a tapered and colletted portion having an interior chamber, in which the curvate head is initially polyaxially disposed. A locking collar is disposed around a tapered and colletted portion, such that translation thereof in the direction of the expanding taper causes the interior volume to contract onto the curvate head and lock it therein. The interior surface of the locking collar also includes a taper.

WO 2007/038350 A2 describes an apparatus for connecting a bone anchor to a support rod that includes a connector body and a cap. The connector body has a channel to receive and locate the support rod relative to the bone anchor. A sleeve fits over a socket portion of the connector body to lock the bone anchor in the socket. The connector body has a lower section with an exterior surface which is at least part-spherical. The sleeve has a conical inner surface, which is slideable over the outer surface of the lower section of the socket to compress the socket to lock the bone anchor relative to the connector body.

SUMMARY

It is an object of the invention to provide a receiving part for receiving a rod for coupling the rod to a bone anchoring element, and a bone anchoring device with such a receiving part, which is improved with respect to safety in use.

The bone anchoring device has improved safety since it exhibits a greater locking force compared to a bone anchoring device which clamps the head using at least one tapered surface portion at the head receiving portion or the locking ring. The greater locking force is achieved in that the cooperating surfaces of the receiving part and the locking ring are configured to create a clamping force during vertical movement on the locking ring that is perpendicular to the central axis of the receiving part.

The enhanced locking force is achieved with a compact and low profile design of the bone anchoring device, in particular with respect to a maximum outer diameter of the bone anchoring device. Furthermore, the bone anchoring device includes simple mechanical elements that can be easily manufactured. The bone anchoring device may also have a pre-locking function, where the locking ring holds the head in the head receiving portion such that the head can pivot relative to the head receiving portion but cannot be removed from the head receiving portion.

In addition, the head may be held in the head receiving portion by applying a small pre-load to frictionally clamp the head, so that the head can only pivot relative to the head receiving portion by applying a three greater than the friction force to one of the components.

Furthermore, with the bone anchoring device, a modular system can be provided with various bone anchors that can be mounted to the receiving part easily prior to surgery.

BRIEF DESCRIPTION OF THE DRAWINGS

Further features and advantages of the invention will become apparent from the description of embodiments using the accompanying drawings. In the drawings.

DETAILED DESCRIPTION

Figure 1:
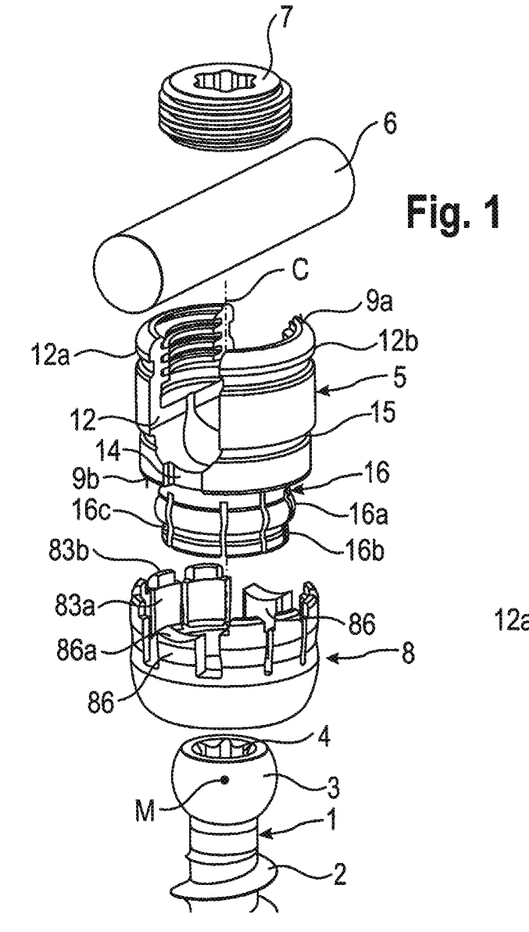
FIG. 1 shows a perspective exploded view of a bone anchoring device according to a first embodiment of the present invention.
Figure 2:
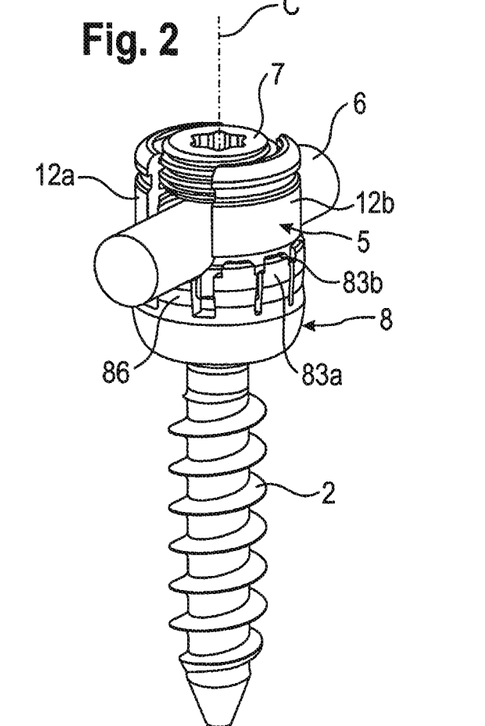
FIG. 2 shows a perspective view of the bone anchoring device of FIG. 1 in an assembled state.

As shown in FIGS. 1 and 2, a bone anchoring device according to a first embodiment of the present invention includes a bone anchoring element 1 in the form of a bone screw having a threaded shaft 2 and a spherical segment-shaped head 3 with a center M of the sphere. The head 3 has a recess 4 for engagement with a driver or tool. The bone anchoring device further includes a receiving part body 5 for receiving a rod 6 to connect the rod to the bone anchoring element 1. Further, a closure element 7 in the form of, for example, an inner screw or set screw is provided for securing the rod 6 in the receiving part body 5. In addition, the bone anchoring device includes a locking ring 8 for locking the head 3 in the receiving part body 5. The receiving part body 5 and the locking ring 8 form a receiving part.

As further shown in FIGS. 3 to 5 and 9a to 9c, the receiving part body 5 includes a rod receiving portion 9, which has a first end 9a and a second end 9b opposite the first end 9a. The rod receiving portion 9 is substantially cylindrical and has a coaxial first bore 10 extending from the first end 9a to the second end 9b and a central axis C. A diameter of the first bore 10 is smaller than a greatest diameter of the head 3 of the bone anchoring element 1. The rod receiving portion 9 also has a coaxial second bore 11 extending from the first end 9a to a distance from the second end 9b. A diameter of the second bore 11 is larger than the diameter of the first bore 10 and larger than a diameter of the rod 6. A U-shaped recess 12 is provided in the rod receiving portion 9 that extends from the first end 9a in the direction of the second end 9b. The U-shaped recess 12 forms a channel for the rod 6, and has a size such that the rod 6 can be placed and guided therein. By means of the U-shaped recess 12, two free legs 12a, 12b are formed, on which an internal thread 13 is provided. The internal thread can be a metric thread, a flat thread, a negative angle thread, a saw-tooth thread, or any other thread form. Preferably, a thread form such as a flat thread or a negative angle thread is used, which prevents or reduces splaying of the legs 12a, 12b when the inner screw 7 is screwed-in. The depth of the U-shaped recess 12 is such that the rod 6 and the inner screw 7 can be inserted between the legs 12a, 12b.

Figure 3:
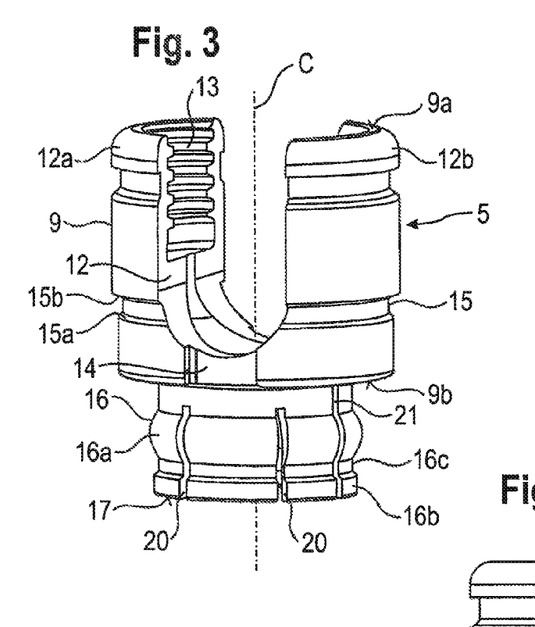
FIG. 3 shows a perspective view of a receiving part body of the bone anchoring device according to the first embodiment.
Figure 4:
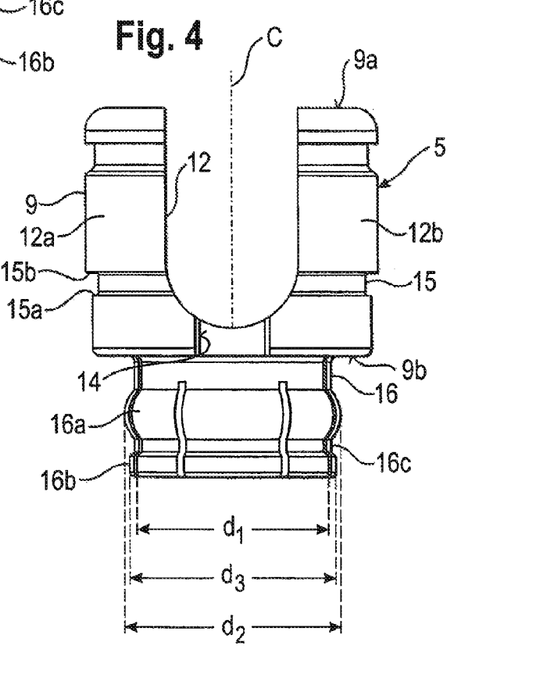
FIG. 4 shows a side view of the receiving part body of FIG. 3.
Figure 5:
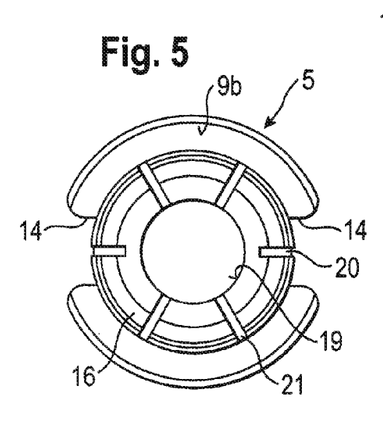
FIG. 5 shows a bottom view of the receiving part body of FIG. 3.
Figures 6, 7, 8:
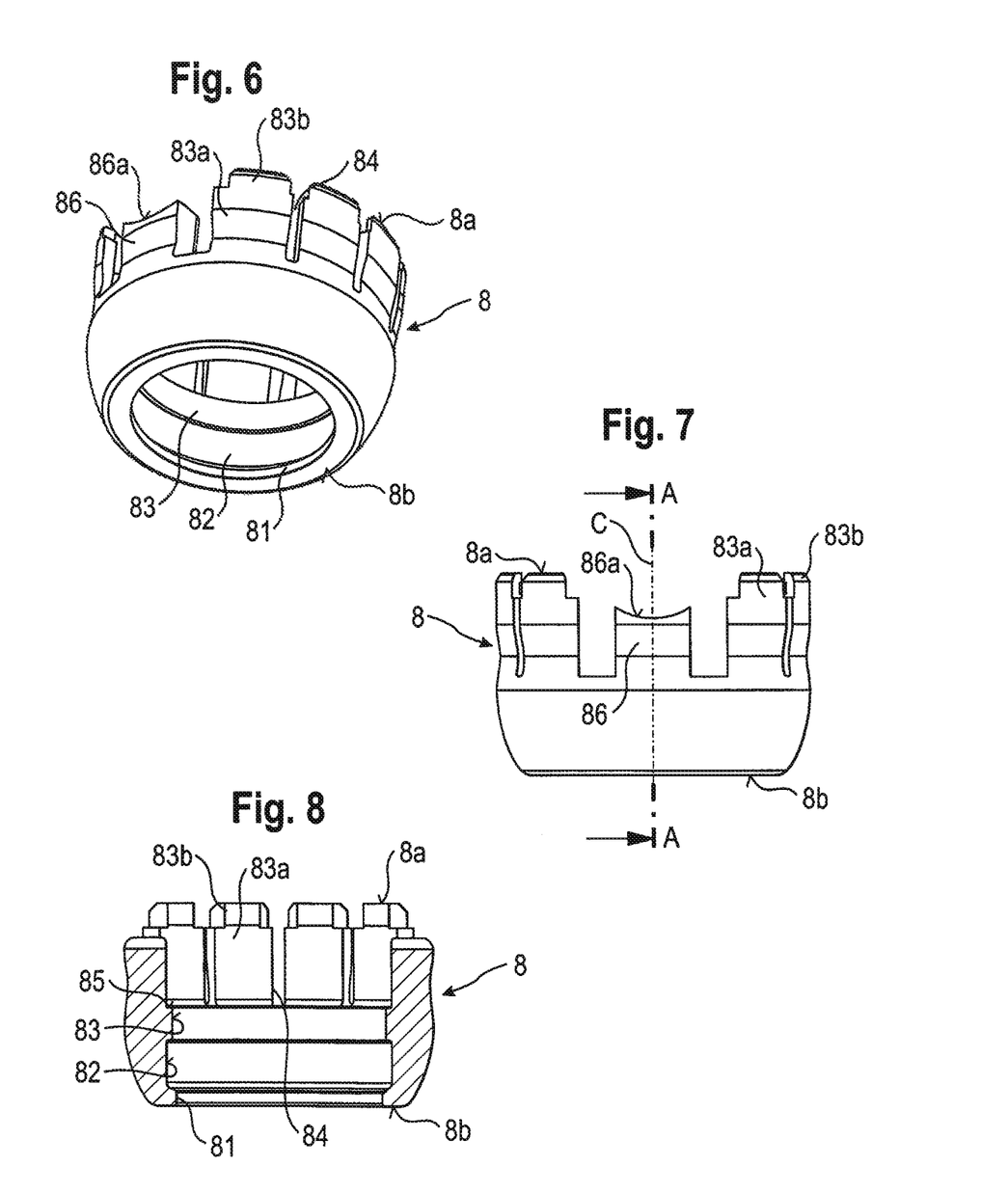
FIG. 6 shows a perspective view of a locking ring of the bone anchoring device according to the first embodiment.
FIG. 7 shows a side view of the locking ring of FIG. 6.
FIG. 8 shows a cross-sectional view of the locking ring of FIGS. 6 and 7 along line A-A in FIG. 7.

At either end of the U-shaped recess 12 seen in a direction along the channel axis, cutouts 14 extend from the second end 9b to the bottom of the U-shaped recess 12.

In the outer surface of the rod receiving portion 9 in the region of the legs 12a, 12b a groove 15 is provided, which extends in a circumferential direction and serves for engagement with a portion of the locking ring 8. The groove 15 is asymmetric in such a way that it allows a disengagement of the locking ring and the groove when the locking ring 8 is shifted downwards. The asymmetric shape of the groove may be realized by a downwardly inclined lower wall 15a and an upper wall 15b having a surface substantially perpendicular to central axis C. Between the groove 15 and the second end 9b the diameter of the rod receiving portion 9 may be slightly reduced compared to other portions of the rod receiving portion 9.

Adjacent to the second end 9b, the receiving part body 5 further includes a head receiving portion 16 providing an accommodation space for the head 3 of the bone anchoring element 1. The head receiving portion 16 has a free end 17 on a side opposite to the second end 9b of the rod receiving portion 9. A maximum outer diameter of the head receiving portion 16 is smaller than a maximum outer diameter of the rod receiving portion 9, so that the head receiving portion 16 is recessed with respect to the rod receiving portion 9. The head receiving portion 16 has an internal hollow section 18, which is spherically-shaped with a radius matching the radius of the head 3 of the bone anchoring element. The internal hollow section 18 has an opening 19 at the free end 17. The dimensions of the internal hollow section 18 are such that the hollow section 18 encompasses the head 3 of the bone anchoring element 1, including at least a region of the largest diameter of the head 3. When the head 3 is introduced into the internal hollow section 18, its center M lies substantially on the central axis C.

Slits 20 are provided in the head receiving portion 16, which are open to the free end 17 and extend to a distance from the second end 9b of the rod receiving portion 9. The slits 20 have at least such a length that they include or encompass a region of the largest inner diameter of the internal hollow section 18. Other slits 21 may extend from the free end 17 to the second end 9b of the rod receiving portion 9. The slits 20 and/or 21 in the head receiving portion 16 render the head receiving portion 16 flexible, such that the head 3 of the bone anchoring element 1 can be inserted in the head receiving portion 16 by expanding the head receiving portion 16, and can be clamped therein by compressing the head receiving portion 16.

As best seen in FIG. 4, an outer surface of the head receiving portion is generally cylindrical with an outer diameter $d_1$. At a distance from the second end 9b of the rod receiving portion 9, an exterior surface portion in the form a ring-shaped bulge 16a with a largest outer diameter $d_2$ that is greater than $d_1$ is provided. The ring-shaped bulge 16a includes or encompasses a region of the largest inner diameter of the internal hollow section 18. The cross-section of the ring-shaped bulge 16a may be, for example, a section of a circle. However, the cross-section can also be otherwise shaped, for example, a section of an ellipsoid, or for example, asymmetric in an axial direction. Adjacent to the free end 17, a cylindrical portion 16b is formed that has an outer diameter $d_3$ that is greater than $d_1$ and smaller than or equal to $d_2$. Hence, between the ring-shaped bulge 16a and the cylindrical portion 16b, a groove 16c may be formed. An upper edge of the cylindrical section 16b may be chamfered to facilitate engagement with the locking ring 8 described below.

The locking ring will now be described with reference to FIGS. 6 to 9c. The locking ring 8 is substantially cylindrical and has an upper end 8a and a lower end 8b. In a mounted state, the upper end 8a is oriented in a direction of the first end 9a of the rod receiving portion 9, and the lower end 8b is oriented towards the free end 17 of the head receiving portion 16.

Figure 9A:
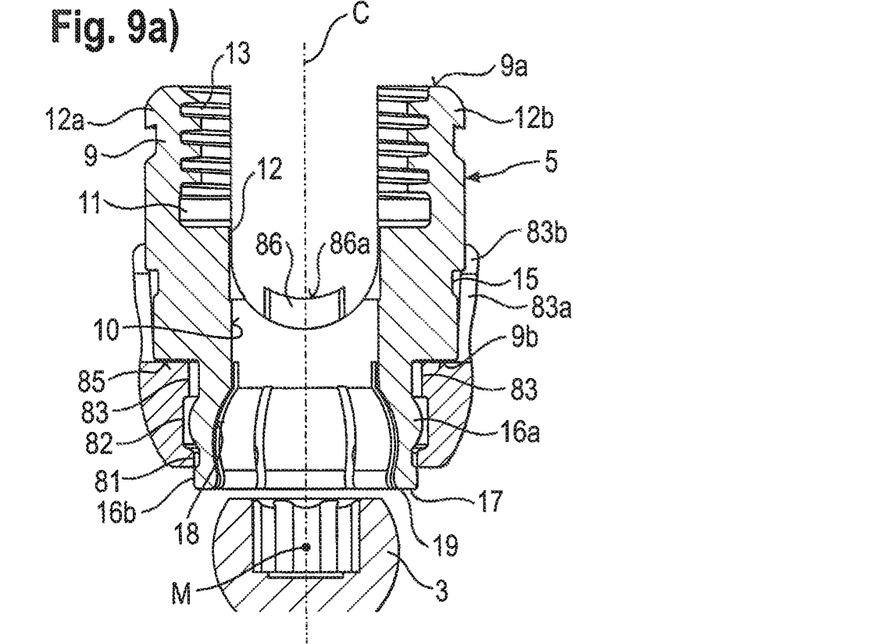
FIG. 9a shows a cross-sectional view of the bone anchoring device of the first embodiment in a first position, in which the head can be introduced into the receiving part.

Adjacent the lower end 8b, the locking ring 8 has a first hollow cylindrical portion 81 with a surface having an inner diameter that is slightly smaller than the outer diameter of the cylindrical portion 16b of the head receiving portion 16, in such a way that the cylindrical portion 81 of the locking ring 8 and the cylindrical portion 16b of the head receiving portion 16 can engage in an interference-fit connection. A height of the cylindrical portion 81 is such that the cylindrical portion 81 can engage or fit in the groove 16c of the head receiving portion 16. Adjacent to the first hollow cylindrical portion 81, there is a second hollow cylindrical portion 82 with a surface having an inner diameter that is greater than the outer diameter $d_2$ of the ring-shaped bulge 16a of the head receiving portion 16, to such an extent that in a first position of the locking ring 8, which is shown in FIG. 9a, the ring-shaped bulge 16a can extend into the second hollow cylindrical portion 82 of the locking ring 8, and has space for expansion in a radial direction. A height of the second hollow cylindrical portion 82 may be about the height of the ring-shaped bulge 16a in an axial direction.

Figure 9B:
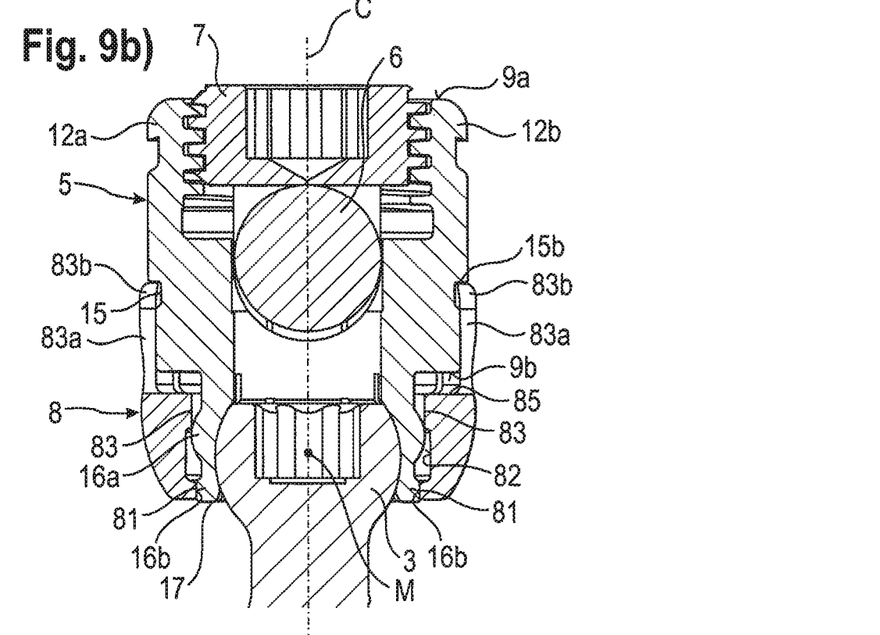
FIG. 9b shows a cross-sectional view of the bone anchoring device of the first embodiment in a second position, in which the head is introduced into receiving part and the locking ring is in a pre-locking position.
Figure 9C:
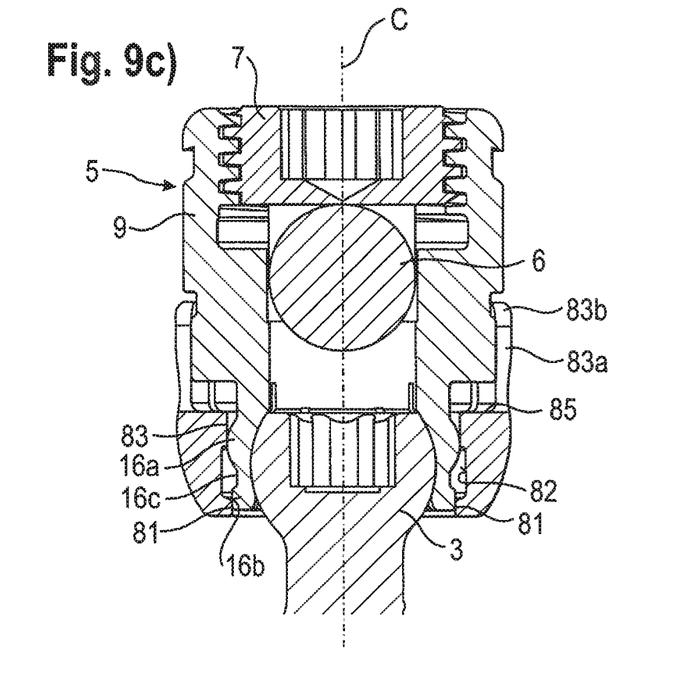
FIG. 9c shows a cross-sectional view of the bone anchoring device where a rod is inserted and an angular position of the screw is locked by the locking ring in a locking position.

Following the second hollow cylindrical portion 82, a third hollow cylindrical portion 83 is provided. The inner diameter of a surface corresponding to the third hollow cylindrical portion 83 is slightly smaller than the greatest outer diameter $d_2$ of the ring-shaped bulge 16a of the head receiving portion 16, such that when the cylindrical portion 83 cooperates with the ring-shaped bulge 16a, an interference-fit connection is achieved. A height of the third hollow cylindrical portion 83 is such that when the locking ring 8 is in a lowermost position, as shown in FIG. 9c, the third hollow cylindrical portion 83 is in contact with at least the area of the greatest outer diameter of the ring-shaped bulge 16a.

The locking ring 8 further includes upwardly extending flexible wall portions 83a which are separated from each other by slits 84. The upwardly extending wall portions 83a are arranged at an outer circumference of an inner circumferential shoulder 85 of the locking ring 8, and render the locking ring 8 flexible in its upper region. The number and size of the slits 84 and the thickness of the wall portions 83a are configured such that a desired flexibility is obtained. At a free end the wall portions 83a may include engagement sections 83b, which are shaped so as to engage the groove 15 provided on the outer surface of the rod receiving portion 9.

Two projections 86, which are located diametrically opposite to each other, also extend from the shoulder 85. The projections 86 have a height such that they project into the bottom of the U-shaped recess 12 through the cutouts 14 when the locking ring 8 is in a position in which the head 3 is not yet locked, as shown in FIGS. 9a and 9b. A free end surface 86a of the projections 86 can be curved, for example, with a curvature corresponding to a curvature of the rod 6. The locking ring 8 is arranged around the head receiving portion 16 with the projections 86 located at the positions of the U-shaped recess 12. By means of this, the projections 86 prevent the locking ring 8 from rotating when the rod 6 is not yet inserted.

The flexibility of the head receiving portion 16 and the size of the head receiving portion 16 at the open end 17 allows for mounting of the locking ring 8 by assembling the locking ring 8 from the free end 17 onto the head receiving portion 16. An outer diameter of the locking ring 8 may be sized such that the locking ring 8 does not project substantially beyond the rod receiving portion 9 of the receiving part body 5 in a radial direction, to ensure a compact shape of the receiving part.

The inner screw 7 has a thread corresponding to the internal thread 13 provided on the legs 12a, 12b. If a thread form that prevents or reduces the legs from splaying is used, a single fixation element such as the inner screw 7 may be sufficient. This further reduces the size of the bone anchoring device in a radial direction.

The receiving part body 5, the locking ring 8, the inner screw 7, and the bone anchoring element 1 may be made of a bio-compatible material, for example, of titanium or of stainless steel, or of bio-compatible allows such as Nitinol, or of a bio-compatible plastic material, such as polyether-etherketone (PEEK). The parts can be made of the same or of different materials.

The function of the locking ring 8 will now be explained with reference to FIGS. 9a to 9c. As shown in FIG. 9a, a first position of the locking ring 8, which is an insertion position where the locking ring 8 is latched with respect to the receiving part body 5, is arranged in such a way that the first hollow cylindrical portion 81 engages or is adjacent to the groove 16c at the outer surface of the head receiving portion 16. Since the inner diameter of the first hollow cylindrical portion 81 and the inner diameter of the second hollow cylindrical portion 82 are larger than the outer diameter of the head receiving portion 16 at the positions of the groove 16c and the ring-shaped bulge 16a, respectively, an expansion of the head receiving portion 16 is possible when the head is introduced. In a first position, the locking ring 8 is additionally held by a clamping force between the rod receiving portion 9 and the flexible wall portions 83a, which may be slightly bent outwards as can be seen in FIG. 9a.

When the locking ring 8 is in the first position, the head receiving portion 16 is not compressed. In this position, the introduction of the head 3 of the bone anchoring element 1 is possible, as can be seen in FIG. 9a. In the first position, the locking ring 8 is prevented from moving further upwards towards the first end 9a of the rod receiving portion 9, since the shoulder 85 of the locking ring 8 abuts against the second end 9b of the rod receiving portion 9.

After introduction of the head 3, the locking ring 8 is moved downwards in an axial direction into a second position where the locking ring 8 is latched with respect to the receiving part body 5 in a pre-locking position, as shown in FIG. 9b. In the second position, the locking ring 8 has been shifted towards the free end 17 of the head receiving portion 16, until the engagement portions 83b of the flexible wall portions 83a resiliently snap into the groove 15 provided at the rod receiving portion 9. The free upper edge of the engagement portions 83b may abut against the upper wall 15b of the groove 15, thereby preventing upward movement of the locking ring 8 out of the pre-locking position back toward the insertion position. On the other hand, the inclined lower wall 15a of the groove 15 prevents inadvertent downward movement of the locking ring 8 towards the free end 17, but allows such downward movement upon exertion of an additional force.

In the second position as shown in FIG. 9b, the first hollow cylindrical portion 81 slightly compresses the cylindrical portion 16b of the head receiving portion in an interference-fit manner, so that the head 3 is prevented from removal out of the hollow internal section 18. In addition, the third hollow cylindrical portion 83 may begin to engage the ring-shaped bulge 16a, so as to slightly compress the head receiving portion 16, thereby further contributing to prevention of removal of the head 3. In addition, in some embodiments, the dimensions of the engaging portions can be defined such that in the second position, as shown in FIG. 9b, the head 3 is held in the hollow internal section 18 by friction in an adjustable angular position, so that the head 3 can still be pivoted relative to the receiving part body 5 by applying a force greater than the friction force.

Figure 9D:
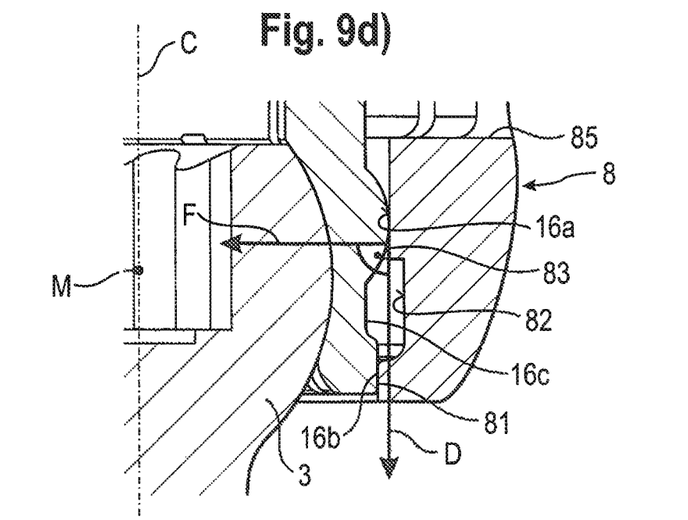
FIG. 9d shows an enlarged portion of FIG. 9c.

A third position, which is a locking position, is shown in FIG. 9c where the locking ring 8 has been moved further axially downwards. In the third position, the head 3 is finally locked within the head receiving portion 16. The inner surfaces of the first hollow cylindrical portion 81 and the third hollow cylindrical portion 83 respectively engage the cylindrical portion 16b and the ring-shaped bulge 16a in an interference-fit manner, thereby firmly compressing the head receiving portion 16 around the head 3. The head 3 is locked by exerting pressure at two defined circumferential areas, one at a central portion of the ring-shaped bulge 16a, which may be slightly above an area of the head 3 with the greatest diameter, and another at the cylindrical portion 16b, which is below the area of the head 3 with the greatest diameter. The clamping force, as shown in FIG. 9d by the arrow F that acts onto the head receiving portion 16 when the locking ring 8 is moved in the direction indicated by arrow D, is perpendicular to the central axis C of the receiving part body 5. Thereby, the force acting in the locking position onto the head may be enhanced compared to a device that uses tapered surface portions. The movement of the cooperating surfaces is a vertical movement coaxial to the central axis. Therefore, the force flow is predictable. The shapes of the cooperating surfaces are easy to manufacture.

In some embodiments, the bone anchoring device may be pre-assembled as follows. First, the locking ring 8 is mounted onto the receiving part body 5 from the free end 17. This can be done, for example, by a manufacturer. Preferably, the locking ring 8 is initially in the insertion position. Thereafter, the head 3 of the anchoring element 1 can be introduced from the free end 17 into the hollow internal portion 18 of the head receiving portion 16. Thereafter, the locking ring 8 can be moved downwards into the pre-locking position.

During surgery, a pre-assembled bone anchoring device may be screwed into bone. The recess 4 of the head 3 can be accessed with a driver or tool through the first bore 10 of the receiving part body 5. If the head 3 is held in an adjustable angular position by friction in the pre-locking position, an additional force can be exerted onto the receiving part, either manually or by application of an instrument, to align the receiving part with respect to the rod 6. Once a desired position of the bone anchoring devices with respect to the rod 6 is achieved, the inner screw 7 is tightened into the receiving part body 5. When the rod 6 abuts onto the projections 86 of the locking ring 8, the locking ring 8 is shifted downwards into the locking position. Final tightening of the inner screw 7 locks the rod 6 and the head 3 simultaneously.

Figure 10:
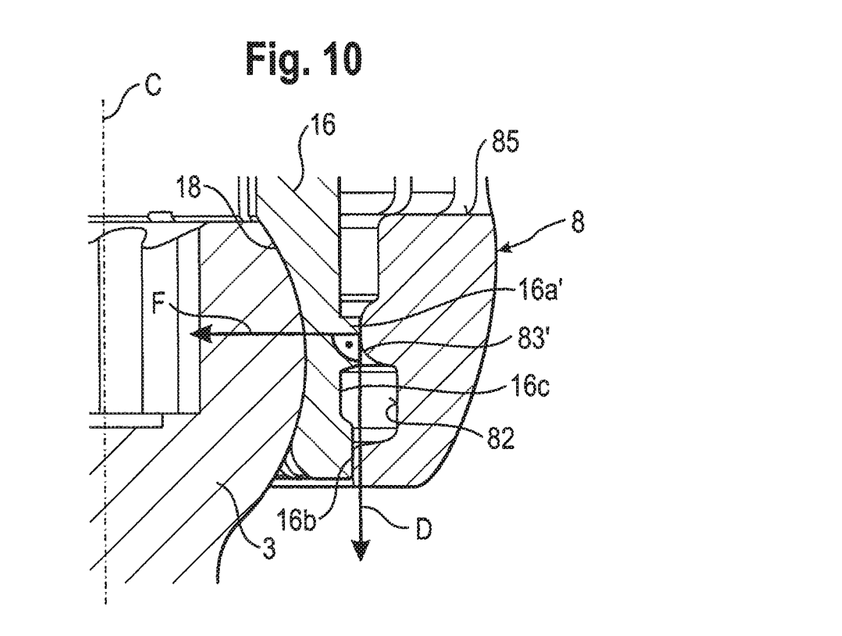
FIG. 10 shows an enlarged section of a cross-sectional view of a bone anchoring device according to a second embodiment of the present invention.

A second embodiment of the bone anchoring device is shown in FIG. 10. A bone anchoring device according to the second embodiment differs from the bone anchoring device according to the first embodiment in the design of the exterior surface of the head receiving portion 16 and the interior surface of the locking ring 8. All other parts are the same or similar, and are designated with the same reference numerals, and the descriptions thereof are not repeated. The head receiving portion 16 has, instead of the ring-shaped bulge 16a, a cylindrical surface portion 16a' with a greatest outer diameter $d_2$ which is greater than an outer diameter $d_1$ of the head receiving portion 16 (see, e.g., FIG. 4). The locking ring 8 has, instead of the third hollow cylindrical portion 83, an inwardly projecting ring-shaped bulge 83' with an inner diameter that is slightly smaller than the outer diameter of the cylindrical portion 16a' of the head receiving portion 16, to enable an interference-fit between the two portions. Hence, these cooperating exterior and interior surface portions in the second embodiment are reversed with respect to those of the first embodiment. Also in this embodiment, the locking of the head 3 may be achieved by an interference-fit between the engaging exterior surface portion of the head receiving portion 16 and the interior surface portions of the locking ring 8 at two contact areas that are approximately around a region of the largest diameter of an inserted head 3 or above and/or below the region of the largest diameter of an inserted head 3. Also in this embodiment, the clamping three F is directed perpendicular to the central axis C of the receiving part body 5, resulting in a high locking force in the locking position.

Figure 11:
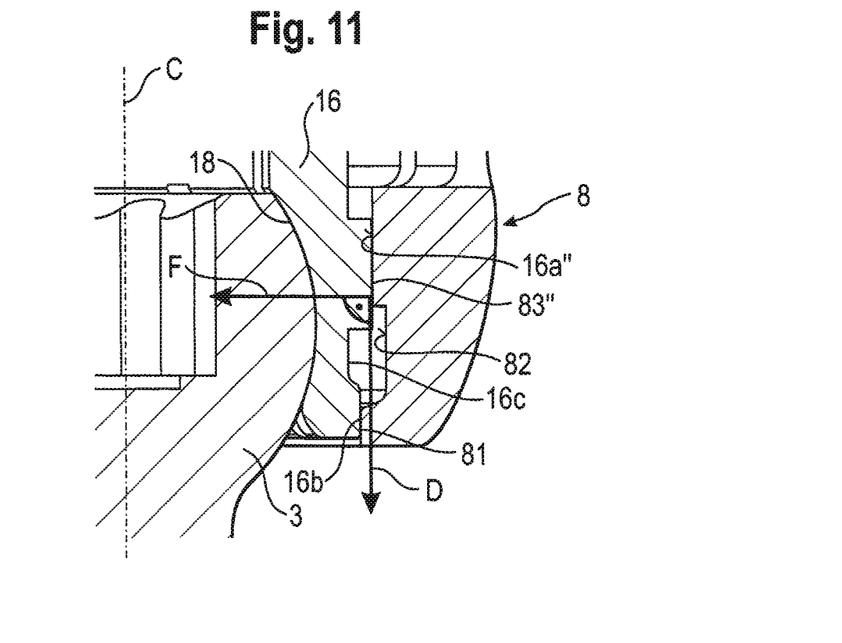
FIG. 11 shows an enlarged section of a cross-sectional view of a bone anchoring device according to a third embodiment of the present invention.

A third embodiment is shown in FIG. 11. Parts which are identical or similar to those of the first and second embodiments are designated with the same reference numerals, and the descriptions thereof are not repeated. The bone anchoring device of the third embodiment also differs from the bone anchoring device of the first and second embodiments in the shape of the exterior surface of the head receiving portion 16 and the interior surface of the locking ring 8. Instead of an engagement between a cylindrical surface and a ring-shaped bulge, an engagement between a first cylindrical surface and a second cylindrical surface is provided. The head receiving portion 16 has a cylindrical surface portion 16a" with an outer diameter $d_2$ that is larger than an outer diameter of the cylindrical portion in the groove 16c". The cylindrical portion 16a" extends in an axial direction over an area that includes a region including a largest outer diameter of an inserted head 3. The locking ring 8 has a third cylindrical portion 83" with an inner diameter that is slightly smaller than the outer diameter of the cylindrical portion 16a", to allow an interference-fit between the portion 16a" and the portion 83". An axial length of the third hollow cylindrical portion 83" is such that it can come into engagement with the cylindrical portion 16a" over a substantial area, including a region of a largest outer diameter of an inserted head 3. The locking of the head 3 in the third embodiment is achieved by exerting a force F onto the head receiving portion 16 via an interference-fit of these cylindrical surfaces. Also in this embodiment, the clamping force is perpendicular to the central axis C. Hence, the locking force that can be achieved may be greater than the locking force that can be achieved with engaging surfaces including a tapered portion.

Various other modifications of the embodiments are possible. For example, the lower engaging surfaces at the free end of the head receiving portion can be omitted. That means, for locking the head, it may be sufficient to provide engaging surfaces in only one circumferential area. In this case, the engaging surfaces should cover a region of the largest diameter of an inserted head. The pre-locking function can be otherwise realized by engagement of portions of the locking ring with other portions of the receiving part body. The ring-shaped bulge portion may also have interruptions in a circumferential direction.

A shape of the receiving part body is also not limited to the embodiments shown. For example, in the rod receiving portion, there can also be slits provided:

A head of the bone anchoring element can have any other shape, such as, for example, a cylindrical shape, whereby a monoaxial bone screw is provided, allowing for rotation of the bone anchoring element with respect to the receiving part around a single axis.

Projections of the locking ring that engage the rod can also have other shapes, for example, a surface of the free end of the projections can be flat or can be otherwise shaped. The projections can also be omitted.

The head receiving portion can have an inclined open end or can be otherwise asymmetric, to allow tier a greater angulation of the head in one direction.

The cylindrical surface portion 16b and the first hollow cylindrical portion 81 can also be replaced, for example, by ring-shaped bulges.

For the bone anchoring element, various different kinds of bone anchoring elements can be used and combined with the receiving part. These anchoring elements include, for example, screws with different lengths, screws with different diameters, cannulated screws, screws with different thread forms, nails, etc. The head of the bone anchoring element and the shaft can also be separate parts, which are connectable to each other.

The channel for the rod can be closed on the first end of the rod receiving portion. In such embodiments, other types of closure elements, such as outer nuts, can be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
    a receiving part body comprising:

a rod receiving portion with a channel for receiving the rod; and a head receiving portion defining an accommodation space for accommodating a head of the bone anchoring element, the head receiving portion having an open end, a central axis extending through the open end, and a flexible region to allow introduction and clamping of the head, wherein the flexible region has a first exterior surface portion positioned along the central axis between the rod receiving portion and a greatest diameter of the accommodation space and a second exterior surface portion positioned along the central axis between the greatest diameter of the accommodation space and the open end; and a locking ring configured to be arranged around the head receiving portion, wherein when the locking ring is around the head receiving portion in an insertion position, at least a portion of an interior surface of the locking ring is aligned axially with and spaced apart radially from the flexible region of the head receiving portion to facilitate expansion of the flexible region for introducing the head;

wherein the locking ring has a first interior surface portion configured to move axially from the insertion position towards the open end of the head receiving portion to engage the first exterior surface portion of the head receiving portion at a first contact region to lock an angular position of the head relative to the head receiving portion, and a second interior surface portion configured to engage the second exterior surface portion of the head receiving portion at a second contact region, wherein the first interior surface portion is spaced apart from an end of the locking ring positioned closer to the open end of the head receiving portion when the locking ring is around the head receiving portion; and wherein at the first contact region, one of the first exterior surface portion and the first interior surface portion comprises a cylindrical surface, and the other one of the first exterior surface portion and the first interior surface portion comprises another cylindrical surface or a ring-shaped bulge portion.

2. A receiving part for receiving a rod for coupling the rod to a bone anchoring element, the receiving part comprising:

a receiving part body comprising:

a rod receiving portion with a channel for receiving the rod; and a head receiving portion defining an accommodation space for accommodating a head of the bone anchoring element, the head receiving portion having an open end, a central axis extending through the open end, and a flexible region to allow introduction and clamping of the head, wherein the flexible region has a first exterior surface portion positioned along the central axis between the rod receiving portion and a greatest diameter of the accommodation space, a second exterior surface portion positioned along the central axis between the greatest diameter of the accommodation space and the open end, and a groove between the first exterior surface portion and the second exterior surface portion; and a locking ring configured to be arranged around the head receiving portion, wherein the head receiving portion is expandable for introducing the head when the locking ring is around the head receiving portion in an insertion position, the locking ring having a first interior surface portion configured to move axially from the insertion position towards the open end of the head receiving portion to engage the first exterior surface portion of the head receiving portion at a first contact region to lock an angular position of the head relative to the head receiving portion, and a second interior surface portion configured to engage the second exterior surface portion of the head receiving portion at a second contact region, wherein the first interior surface portion is spaced apart from an end of the locking ring positioned closer to the open end of the head receiving portion when the locking ring is around the head receiving portion;

wherein at the first contact region, one of the first exterior surface portion and the first interior surface portion comprises a cylindrical surface, and the other one of the first exterior surface portion and the first interior surface portion comprises another cylindrical surface or a ring-shaped bulge portion.

3. The receiving part of claim 2, wherein a smallest inner diameter of the first interior surface portion is smaller than a largest outer diameter of the first exterior surface portion to achieve an interference-fit connection at the first contact region.

4. The receiving part of claim 2, wherein the second interior surface portion of the locking ring is spaced apart from the first interior surface portion in an axial direction.

5. The receiving part of claim 2, wherein the second exterior surface portion comprises a cylindrical surface.

6. The receiving part of claim 2, wherein the second interior surface portion comprises a cylindrical surface.

7. The receiving part of claim 2, wherein the second contact region is configured to be closer to the central axis in a radial direction than the first contact region.

8. The receiving part of claim 2, wherein the second contact region is configured to be a same distance from the central axis as the first contact region.

9. The receiving part of claim 2, wherein the second contact region is configured to be adjacent to the open end of the head receiving portion.

10. The receiving part of claim 2, wherein when the locking ring is in the insertion position, the second interior surface portion of the locking ring is positioned adjacent to the groove.

11. The receiving part of claim 2, wherein the first exterior surface portion and the second exterior surface portion both comprise cylindrical surfaces.

12. The receiving part of claim 2, wherein the first exterior surface portion comprises the ring-shaped bulge portion and the first interior surface portion comprises the cylindrical surface.

13. The receiving part of claim 2, wherein the first exterior surface portion comprises the cylindrical surface and the first interior surface portion comprises the ring-shaped bulge portion.

14. The receiving part of claim 2, wherein when the locking ring is in a locking position where the head is locked in the head receiving portion, the first exterior surface portion contacts the first interior surface portion.

15. The receiving part of claim 2, wherein the locking ring is movable from a position closer to the rod receiving portion towards the open end of the head receiving portion upon exerting a pressure onto the locking ring via the rod.

16. The receiving part of claim 2, wherein the rod receiving portion has a first end, a second end adjacent to the head receiving portion, and a recess extending from the first end in the direction of the second end forming the channel for the rod.

17. The receiving part of claim 2, wherein the rod receiving portion has a first end and a second end, wherein the head receiving portion is adjacent to the second end, and wherein an outer diameter of the head receiving portion at the second end is smaller than a diameter of the rod receiving portion at the second end.

18. A bone anchoring device comprising:
a bone anchoring element comprising a shaft for anchoring in a bone and a head; and
a receiving part comprising:
a receiving part body comprising a rod receiving portion with a channel for receiving a rod, and a head receiving portion defining an accommodation space for accommodating the head, the head receiving portion having an open end, a central axis extending through the open end, and a flexible region to allow introduction and clamping of the head, wherein the flexible region has a first exterior surface portion positioned along the central axis between the rod receiving portion and a greatest diameter of the accommodation space, a second exterior surface portion positioned along the central axis between the greatest diameter of the accommodation space and the open end, and a groove between the first exterior surface portion and the second exterior surface portion; and
a locking ring configured to be arranged around the head receiving portion, wherein the head receiving portion is expandable for introducing the head when the locking ring is around the head receiving portion in an insertion position, the locking ring having a first interior surface portion configured to move axially from the insertion position towards the open end of the head receiving portion to engage the first exterior surface portion of the head receiving portion at a first contact region to lock an angular position of the head relative to the head receiving portion, and a second interior surface portion configured to engage the second exterior surface portion of the head receiving portion at a second contact region, wherein the first interior surface portion is spaced apart from an end of the locking ring positioned closer to the open end of the head receiving portion when the locking ring is around the head receiving portion;
wherein at the first contact region, one of the first exterior surface portion and the first interior surface portion comprises a cylindrical surface, and the other one of the first exterior surface portion and the first interior surface portion comprises another cylindrical surface or a ring-shaped bulge portion.

19. The bone anchoring device of claim 18, wherein the head has an exterior surface portion which is spherically-shaped.

20. The bone anchoring device of claim 18, further comprising a closure element for securing the rod in the channel.

21. The bone anchoring device of claim 20, wherein the closure element comprises an inner screw.

22. A method of coupling a rod to a bone or vertebra via a bone anchoring device, the bone anchoring device comprising an anchoring element having a shaft for anchoring in the bone or vertebra and a head, and a receiving part comprising a receiving part body comprising a rod receiving portion with a channel for receiving the rod, and a head receiving portion defining an accommodation space for accommodating the head, the head receiving portion having an open end, a central axis extending through the open end, and a flexible region to allow introduction and clamping of the head, wherein the flexible region has a first exterior surface portion positioned along the central axis between the rod receiving portion and a greatest diameter of the accommodation space, a second exterior surface portion positioned along the central axis between the greatest diameter of the accommodation space and the open end, and a groove between the first exterior surface portion and the second exterior surface portion, and a locking ring configured to be arranged around the head receiving portion, wherein the head receiving portion is expandable for introducing the head when the locking ring is around the head receiving portion in an insertion position, the locking ring having a first interior surface portion and a second interior surface portion, wherein the first interior surface portion is spaced apart from an end of the locking ring positioned closer to the open end of the head receiving portion when the locking ring is around the head receiving portion, wherein one of the first exterior surface portion and the first interior surface portion comprises a first cylindrical surface, and the other one of the first exterior surface portion and the first interior surface portion comprises a second cylindrical surface or a ring-shaped bulge portion, the method comprising:
inserting the bone anchoring device into the bone or vertebra;
adjusting an angular position of the receiving part relative to the bone anchoring element;
inserting the rod into the channel; and
advancing a closure element into the channel to push the rod against the locking ring and to move the locking ring towards the open end of the head receiving portion to a locking position where the first cylindrical surface engages the second cylindrical surface or the ring-shaped bulge portion at a first contact region to lock an angular position of the head relative to the head receiving portion, and the second interior surface portion engages the second exterior surface portion at a second contact region.

* * * * *